United States Patent [19]

Morris

[11] Patent Number: 4,797,101
[45] Date of Patent: Jan. 10, 1989

[54] DENTAL IDENTIFICATION SYSTEM

[76] Inventor: Alvan Morris, 7148 Loch Lomond Dr., Bethesda, Md. 20817

[21] Appl. No.: 24,487

[22] Filed: Mar. 11, 1987

[51] Int. Cl.⁴ .............................................. A61C 5/00
[52] U.S. Cl. ..................... 433/229; 433/215
[58] Field of Search ................. 433/229, 50, 53, 56, 433/72, 215

[56] References Cited

U.S. PATENT DOCUMENTS

| | | | |
|---|---|---|---|
| Re. 30,594 | 6/1977 | Samis . | |
| 3,925,896 | 12/1975 | McDowell | 433/229 |
| 4,208,795 | 6/1980 | Muhlemann et al. . | |
| 4,239,261 | 12/1980 | Richardson . | |
| 4,306,866 | 12/1981 | Weissman | 433/215 |
| 4,439,154 | 3/1984 | Mayclin . | |
| 4,512,744 | 4/1985 | Michnick et al. . | |
| 4,557,693 | 12/1985 | Elggren . | |

OTHER PUBLICATIONS

Promotional Literature of Micro I/D Inc., Peoria, Ill., distributed 1985 (?).

Primary Examiner—Larry Jones
Attorney, Agent, or Firm—Pollock, Vande Sande and Priddy

[57] ABSTRACT

A recess is drilled into the buccal face of a tooth of a human subject, and a microdot having identifying information thereon is placed at the bottom of said recess whereafter the recess is filled with a transparent bonding material. When identification of the subject is desired, the microdot is photographed through the transparent filler material to provide a photographic print which contains the identifying information. The camera employed includes a fixture extending forwardly of the lens for accurately locating the camera lens relative to the microdot, the camera having a fixed focus lens whose focal length corresponds to the distance between the lens and the buccal face of the tooth plus the depth of the recess containing the microdot. A special technique, and an associated calibration instrument, are used for drilling the recess in the subject's tooth to a precise depth to assure that a sharp image of the microdot is obtained when the microdot is photographed by the fixed focus camera.

13 Claims, 3 Drawing Sheets

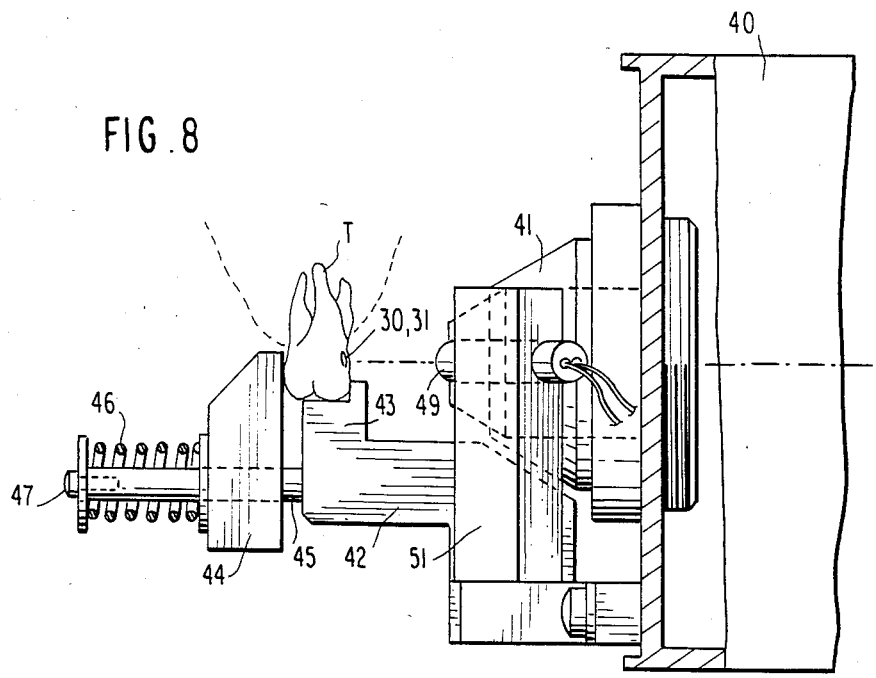
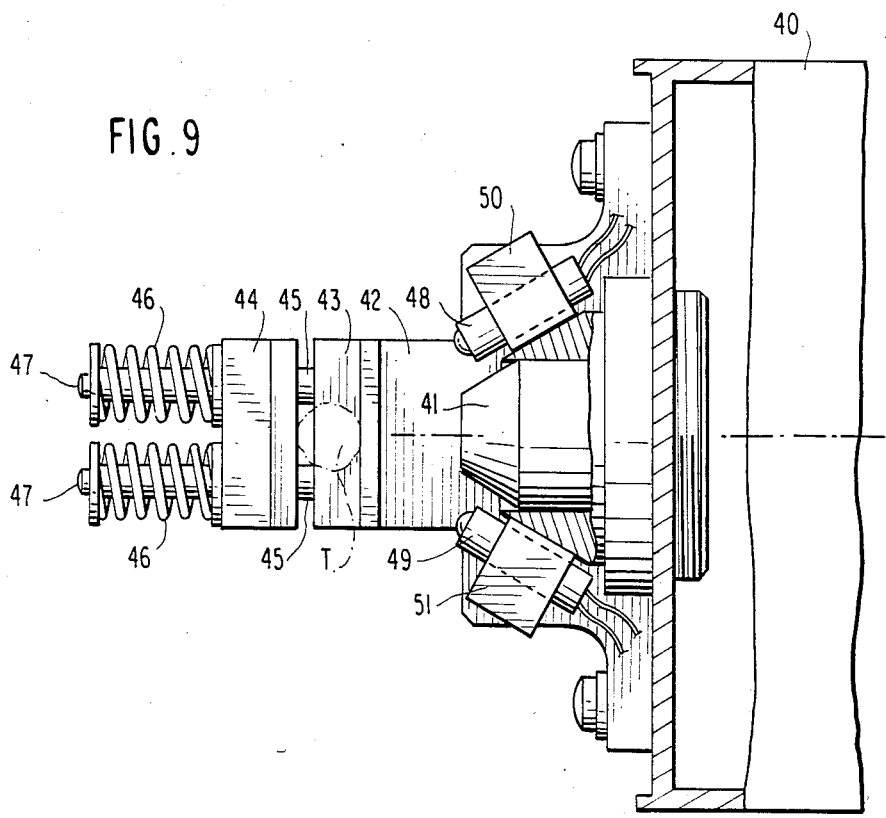

DENTAL IDENTIFICATION SYSTEM

BACKGROUND OF THE INVENTION

A variety of techniques and instrumentalities have been suggested heretofore for intimately associating an identification device of some type with a human subject to provide personal identification of the subject, his or her medical condition, etc. In recent years, an increasingly popular approach has contemplated the provision of such identifying data by the placement of a small information carrier, sometimes taking the form of a photographic microdot, in or on one of the subject's teeth. Prior teachings along this line are found in the following U.S. Pat. Nos.: Samis U.S. Pat. No. Re. 30,594 (originally U.S. Pat. No. 4,027,391), Muhlemann et al 4,208,795, Richardson 4,239,261, Mayclin 4,439,154, Michnick et al 4,512,744 and Elggren 4,557,693.

In those cases where a microdot is used as the identification carrier, prior identification techniques have contemplated that the microdot be read under magnification by an appropriate optical device. When the microdot is simply bonded to the surface of a subject's tooth, the reading process may require that the microdot be removed from the tooth, e.g., by a small chisel, before it is read under magnification. This technique has a number of disadvantages, e.g., the microdot can be removed by anyone improperly wishing to secrete a subject's identity, residual bonding agent tends to obscure or blur information contained in the microdot, and the microdot, once removed from the tooth, cannot be reused due to old bonding agent on the microdot. Prior techniques suggested heretofore wherein the identification carrier or microdot is actually imbedded within a tooth give rise to the still further problem of locating the actual position of the microdot or information carrier so that it can be removed from the tooth for reading.

In an effort to obviate some of the foregoing problems, various instrumentalities have been suggested heretofore for reading a microdot while it remains bonded to or embedded within a subject's tooth. In general, however, the instruments that have been suggested for such purposes are complex, costly, and require careful adjustment to assure that the information on a microdot is properly read. As a result, systems of this type have had limited appeal and have not gone into the widespread use which is required of a truly practical identification system.

The present invention is intended to obviate these disadvantages of the prior art by the provision of an improved dental identification system wherein a microdot is implanted into the tooth of a subject at a location which is predetermined, precise, and accurately repeatable from one to another subject, and wherein the information on a microdot so implanted is read, and a permanent record of the information obtained, by a comparatively inexpensive instrument, i.e., a camera employing a fixed focus lens, which does not require any adjustment or calibration at the time the microdot is read.

SUMMARY OF THE INVENTION

In accordance with the present invention, a microdot is embedded into the tooth of a subject at a precise depth, related to the fixed focal length of the lens of a camera that is subsequently employed to read the information on the microdot, to assure that a sharp readable image of the microdot is produced by the camera. The invention involves a special technique for drilling a recess of very precise depth into the tooth of a subject; mechanisms which are used at the time the recess is prepared to assure that the recess has the desired precise depth, and that said precise depth is repeatable from one to another subject; and a camera which has a fixed focus lens and which also has a fixture thereon for properly positioning the camera and its lens relative to a microdot that is secured within the aforementioned recess.

To provide the recess into which the microdot is embedded, a reference plane is initially established adjacent to the face of a tooth of a human subject to be identified, e.g., by placing a clamp onto the subject's tooth. An end-cutting burr is inserted into a dental handpiece, and the position of said burr in the hand piece is adjusted so that the burr protrudes outwardly of said hand piece by a predetermined fixed distance which is defined, for example, by a cylindrical spacer member placed on the burr, plus the distance between said aforementioned reference plane and the outer face of the tooth, plus the predetermined depth of the recess that is to be drilled into the tooth face. A calibration instrument is provided, and employed during this adjusting procedure, for purposes of defining the recess depth portion of the burr extension from the hand piece.

With the burr so adjusted in position in the dental hand piece, a recess of the desired predetermined depth is drilled into the tooth face, a microdot bearing identifying information thereon is placed at the bottom of said recess, and the microdot is secured in place by filling the remainder of the recess with a light curing, transparent, bonding medium. The embedded microdot serves as a permanent identification of the subject, and its location is precisely the same from one subject to another, always being at a known distance from the buccal face of the subject's tooth corresponding to the predetermined depth of the recess.

When it is desired to identify the subject and/or to provide a permanent record of the information present on the microdot embedded in the subject's tooth, the microdot is photographed and magnified by a Polaroid camera that has a fixed focus lens, and that also has a fixture thereon for accurately positioning the camera lens relative to the subject's tooth to assure that the lens focuses precisely on the embedded microdot. The camera fixture includes a spring-biased clamp thereon which engages the subject's tooth at the time the microdot is to be photographed, thereby assuring that the camera is restrained against sideways or in-and-out motion relative to the tooth, each of which might result in an unsharp image. The camera fixture further includes lamps for illuminating the microdot through the transparent bonding medium which secures the microdot in place.

BRIEF DESCRIPTION OF THE DRAWINGS

The foregoing objects, advantages, construction and operation of the present invention will become more readily apparent from the following description and accompanying drawings wherein:

FIG. 8 is a side view of a camera and associated positioning fixture used to photograph the embedded microdot; and FIG. 9 is a top view of the camera and fixture shown in FIG. 8.

DESCRIPTION OF THE PREFERRED EMBODIMENTS

Figure 1:
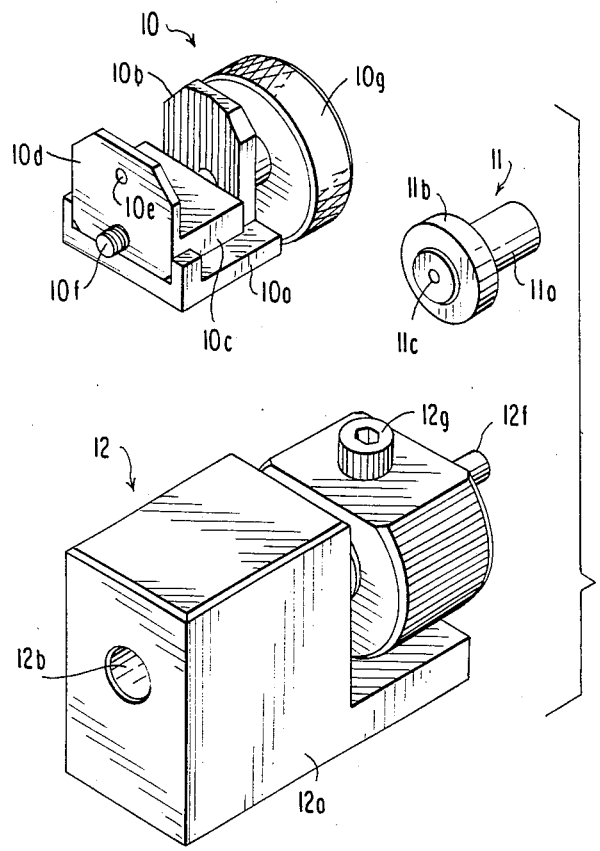
FIG. 1 comprises perspective views of a clamp, spacer, and calibration instrument used with one another to adjust the position of a burr in a dental hand piece.

FIG. 1 illustrates three devices that are employed in the manner to be described hereinafter to adjust the position of a burr in a dental hand piece and to drill a recess of precise, predetermined depth into a face of a subject's tooth. The devices comprise a clamp 10, a spacer 11 and a calibration instrument 12.

Clamp 10 comprises an L-shaped member consisting of a base plate 10a having an integral plate 10b extending upwardly therefrom. The inner surface of plate 10b has a concave configuration, and is striated, so as to provide a configuration which can somewhat conform to and grip the rear surface of a subject's tooth in use. A further L-shaped plate 10c is located on base plate 10a for sliding movement thereon and includes a forward upstanding flange 10d that has a hole 10e therein through which a burr may pass during the adjustment and drilling procedures to be described. A threaded member 10f is in thread engagement with flange 10d, passes through the base of member 10c and through plate 10b and is attached to a knurled knob 10g which may be rotated to vary the spacing between plate 10b and flange 10d. As will become apparent subsequently, the clamp 10 is placed on a subject's tooth with plate 10b adjacent the rear surface of the tooth and flange 10d adjacent a forward or buccal face of the tooth, and is then tightened into place by rotation of knob 10g.

The spacer 11 comprises a plastic element fabricated, e.g., of nylon, consisting of a generally cylindrical portion 11a having a larger diameter cylindrical collar 11b at one end thereof. A bore 11c extends through the spacer 11 along its central axis. Spacer 11 is disposed in surrounding relation to a portion of a burr which extends outwardly of a dental hand piece, and the length of the element 11 defines a predetermined fixed distance by which the burr should extend outwardly of the hand piece.

Figure 2:
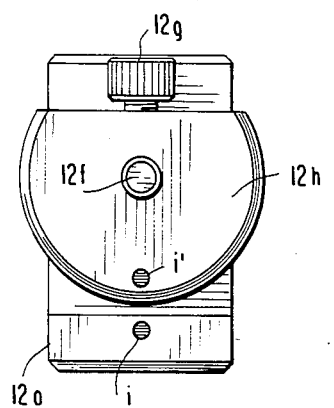
FIG. 2 is an end view of the calibration instrument shown in FIG. 1.

Calibration instrument 12, in addition to being shown in perspective view in FIG. 1, is shown in end view in FIG. 2 and in cross section in FIGS. 5A, 5B, 5C and 5D. The calibration instrument comprises an L-shaped block 12a having a recess 12b at one end thereof which is shaped and sized to receive the cylindrical portion 11a of spacer 11. A channel 12c is provided within block 12a in coaxial relation to recess 12b, the rear end of said channel 12c opening into recess 12b and the forward end of recess 12c opening into a larger interior threaded cavity 12d. A hollow cylindrical sleeve 12e is in thread engagement with the threads in cavity 12d, and includes a pin 12f which is slidable through the hollow center of sleeve 12e in coaxial relation to recess 12b, channel 12c and cavity 12d. Slidable pin 12f may be locked against sliding movement by a set screw 12g which is threaded into a knurled knob portion 12h of sleeve 12e. In addition, a nylon pin 12j is disposed within block 12a in engagement with the threads of sleeve 12e to impose a certain amount of friction on the threads thereby to assure that sleeve 12e remains in the position into which it has been turned. The force with which pin 12j engages the sleeve threads may be adjusted by an Allen-head set screw 12k.

The pitch of the threads employed on sleeve 12e and in block 12a are so selected that when knob 12h is turned through 180°, sleeve 12e is moved axially by the precise distance 0.0125 inches, which is the depth of the recess to be drilled into a subject's tooth. The forward end of block 12a is provided with an indicium i and knob 12h is provided with a further indicium i' (see FIG. 2) which may be used to gauge the extent to which knob 12h is rotated during the adjustment procedure to be described.

Figure 5A:
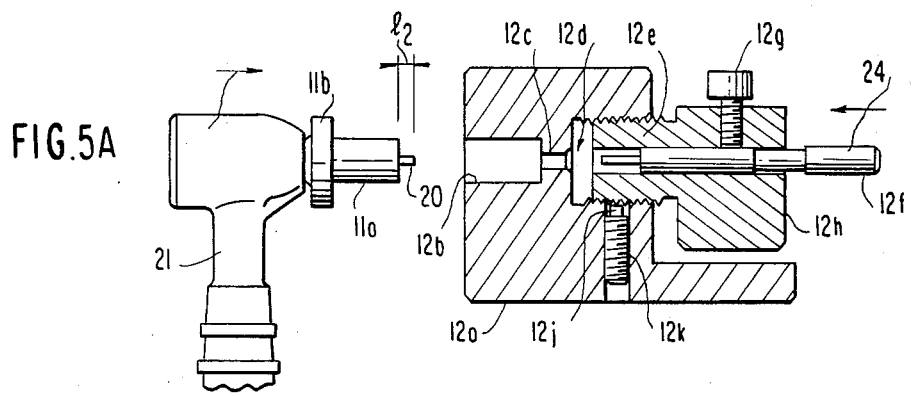
FIGS. 5A, 5B, 5C and 5D depict successive further steps in the burr adjustment procedure, and additionally illustrate in cross section the calibration instrument of FIG. 1 that is used during said adjustment procedure.
Figure 5B:
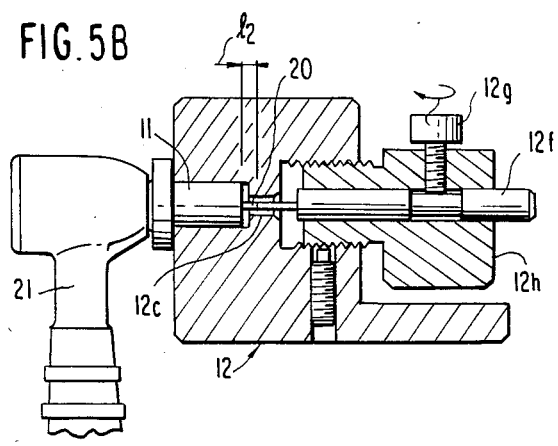
Figure 5C:
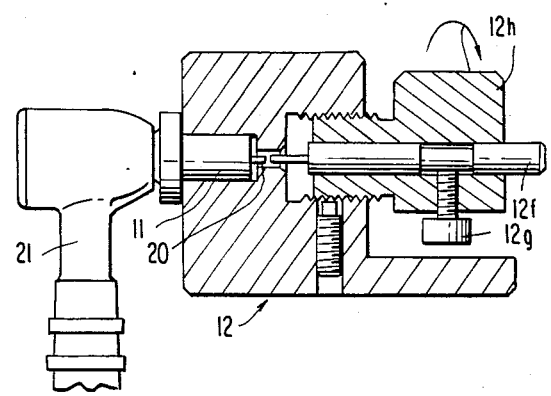
Figure 5D:
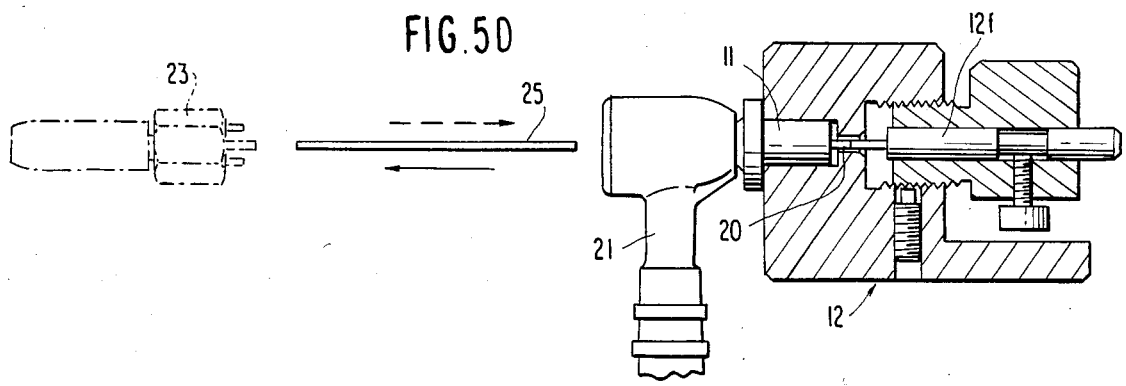
Figure 6:
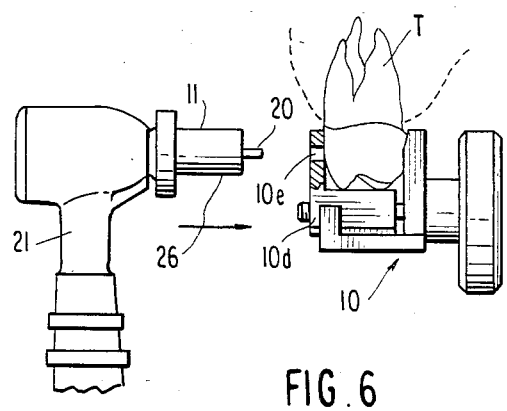
FIG. 6 is a view similar to FIG. 4 showing the step of drilling a recess of precise depth into a subject's tooth.

The manner in which the foregoing instrumentalities are employed will now be described by reference to FIGS. 4, 5 and 6.

Figure 4:
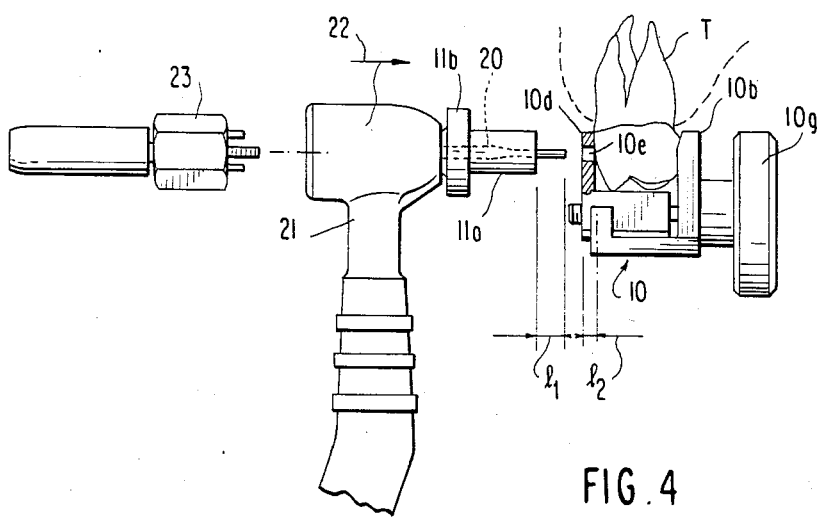
FIG. 4 illustrates the positioning of a subject's tooth in a clamp of the type shown in FIG. 1, and an initial step in the procedure employed to adjust the position of an end-cutting burr in a dental hand piece for purposes of drilling a recess of desired precise depth into a subject's tooth.

Referring to FIG. 4, the clamp 10 is placed on a subject's tooth T with plate 10b in engagement with a rear surface of the tooth and with flange 10d overlying and abutting the facial (buccal) surface of the tooth, and is tightened into place by rotation of knob 10g. The tooth T is preferably an upper molar of the subject since its buccal surface is comparatively flat, and since that surface will not be visible at the conclusion of the procedure to be described hereinafter since the tooth will be covered by the subject's cheek. An end cutting burr 20 is inserted loosely into a high speed dental hand piece 21 so that the burr 20 can be moved longitudinally therein, and the spacer 11 is placed over the burr with collar portion 11b being in engagement with hand piece 21. The burr is initially so disposed in hand piece 21 that it extends forwardly of the portion 11a of spacer 11 by a distance $l_1$ whose length is greater than the distance A ($l_2$) between tooth T and the outer surface of flange 10d. The forwardmost end of the burr is then inserted through hole 10e into contact with the underlying surface of tooth T whereafter hand piece 21 is moved toward the tooth as indicated by arrow 22 until the forwardmost end of spacer 11a engages the outer surface of flange 10d. In the course of this movement, since burr 20 is loose in the dental hand piece, the burr moves rearwardly relative to the hand piece to reduce the forward projecting portion thereof to the length A which corresponds to the thickness of flange 10d (the outer surface of which acts as a reference plane) and any spacing that may exist between the inner surface of flange 10d and the adjacent face of tooth T. The burr, so positioned, is then locked into the hand piece 21 by use of a wrench 23 of known configuration, whereafter the hand piece with the burr locked therein is removed from the vicinity of clamp 10.

The foregoing steps effect a first adjustment of the burr in hand piece 22, the end cutting end of the burr now being located forwardly of the dental hand piece by a predetermined distance that is defined by the length of spacer 11, plus the further distance A that corresponds to the distance between the aforementioned reference plane, i.e., the outer face of flange 10d, and the surface of tooth T. In order to rill a recess having a precise, repeatable depth, i.e., 0.0125 inches, the position of the burr in the hand piece must be further adjusted in a second adjustment step so that it extends forward of the hand piece by the additional length 0.0125 inches. This second adjustment is effected by use of the calibration instrument 12. The procedure is depicted in FIGS. 5A-5D inclusive.

To effect this second adjustment, the dental hand piece, with spacer 11a on burr 20, is moved into engagement with the instrument 12 so that the cylindrical portion 11a of the spacer fills recess 12b in the calibration instrument. The portion of burr 20 that protrudes forward of spacer 11a by the distance A extends into channel 12c as shown in FIG. 5B. Then, with set screw 12g loosened, the portion of central pin 12f forward of knob 12h is grasped manually and moved in a rearward direction as indicated by arrow 24 (FIG. 5A) to cause a reduced diameter rearward end of pin 12f to pass into channel 12c and engage the forward end of burr 20. Pin 12f is then locked into its new position relative to knob 12h by rotation of set screw 12g (FIG. 5B) whereafter knob 12h is turned through a half turn, i.e., 180° to back the rearward end of pin 12f away from the forward end of burr 20 by the precise distance 0.0125 inches (FIG. 5C). The burr 20 is then unlocked from hand piece 21 by use of the aforementioned wrench 23, a metal dowel 25 is inserted into the rear end of the hand piece 21 to push the burr 20 forwardly into engagement with the repositioned pin 12f, the dowel 25 is removed, and the wrench 23 is used to relock the burr into the hand piece at its new position. At this time, the end cutting portion of the burr extends forwardly of spacer 11 by the distance A achieved during the initial adjustment procedure of FIG. 4, plus the additional distance 0.0125 inches achieved by the second adjustment procedure of FIGS. 5A-5D.

Now, with the burr so readjusted, the protruding portion of the burr is inserted into hole 10e in the forward flange 10d of clamp 10 on the subject's tooth T, the hand piece is activated to cause high speed rotation of the burr, and the hand piece 21 is moved forwardly in the direction indicated by arrow 26 until the forwardmost end of spacer 11 again comes into engagement with the aforementioned reference plane, i.e., the outer surface of flange 10d. This operation causes a recess to be drilled into the surface of tooth T which is precisely 0.0125 inches deep and which (by appropriate choice of burr 20) has a diameter slightly greater than the diameter of the microdot that is to be embedded in said recess.

Figure 3:
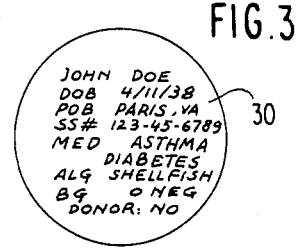
FIG. 3 is an enlarged view of a microdot that is to be embedded in a subject's tooth.
Figure 7:
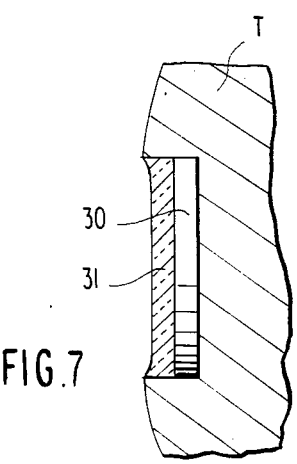
FIG. 7 is an enlarged cross sectional view of a subject's tooth containing an embedded microdot.

A typical microdot, in greatly enlarged form, is shown in FIG. 3. The microdot is a photographic chip of circular configuration having a diameter of about 1.41 mm, and having data thereon in an area of approximately 1.0 mm × 1.0 mm. The microdot itself is preferably white, with the data being impressed thereon by black lettering to make the information noticeable to the maximum extent. The microdot, designated 30, is placed in the bottom of the recess in tooth T prepared by the foregoing procedure in the manner shown in FIG. 7, e.g., by use of a pipette or probe, whereafter the recess is filled and the microdot is covered by a light curing, transparent, bonding medium 31, e.g., the product "Heliobond" distributed by Vivadent (U.S.A.), Inc., of Tonawanda, N.Y. The bonding medium cures quickly, e.g., in about 30 seconds, completing the operation.

In view of the extremely small size of the chip, the data on the chip cannot be read by the naked eye, but has to be read under magnification. The use of a conventional optical instrument for such reading is cumbersome since the subject's head must be held steady for an appreciable length of time to allow the data to be read. In contrast to prior art techniques, therefore, the present invention contemplates that the data on the microdot will be retrieved by use of a camera which is operative to magnify and photograph the microdot thereby to provide an enlarged image which can be read by the naked eye and which, at the same time, provides a permanent record of the microdot information. To simplify the retrieval of information, and to obviate the need to make adjustments in the camera at the time the microdot is photographed, the camera utilizes a lens of predetermined fixed focal length, the depth of the tooth recess achieved by the aforementioned steps having been selected to assure that the microdot is accurately positioned in the focal plane of the camera lens. Moreover, since sidewise motion of the camera during the photographing of the microdot would blur the image, and since in-and-out motion of the camera would result in an unsharp image, the camera includes a fixture thereon extending forwardly of the camera lens for defining the appropriate spacing between the camera lens and the microdot, and for preventing lateral or axial movement of the camera lens relative to the microdot when the photograph is taken.

The camera arrangement is shown in FIGS. 8 and 9 and comprises a camera body 40 which supports a lens 41 and a fixture 42 extending from the camera body forwardly of lens 41. Fixture 42 includes a fixed clamp member 43 which is adapted to engage the forward surface of tooth T adjacent to the embedded microdot 30, 31, and which centers the microdot with the frame of the camera and also sets the precise distance between the microdot and the camera lens so that the microdot is always in focus. Fixture 42 further supports a movable clamp member 44 that is adapted to engage the rear surface of tooth T to stabilize the camera relative to the tooth. The connection between the tooth and fixture cannot be rigid since this might damage the subject's tooth, and therefore clamp member 44 is mounted for movement on a pair of rails 45 and is spring biased into engagement with the rear surface of tooth T by a pair of springs 46 that are disposed in surrounding relation to the rails 45 between clamp member 44 and attachment points 47 at the outermost ends of the rails.

To make the data on the microdot immediately available, a Polaroid camera, and Polaroid film/paper, was selected for use in the preferred embodiment of the invention. The object area to be photographed is, as noted previously, approximately 1.0 mm × 1.0 mm. It is contemplated that the image should be magnified about 26 times, so that the final image is 26 mm × 26 mm. The height of the letters in the microdot itself is about 0.08 mm, the magnified letters then being 2.08 mm high which is readable by the naked eye. Larger magnifications could be used, but the readability would not improve. Should larger magnification be used, moreover, there would be an undesirable reduction in the depth of focus and a requirement for even better centering of the image in the film. It will be understood in this respect that the larger the depth of focus, i.e., the smaller the lens aperture, the less critical becomes the positioning of the camera but more light will be required to effect the same exposure.

The camera used in a preferred embodiment of the present invention utilizes commercially available components. Basically, the CU-5, trigger operated, medical camera system available from Polaroid Corporation, Cambridge, Mass., is used for parts of the camera, the camera body 40 being Polaroid's type 88-1 and the lens and shutter assembly being Polaroid's type 88-17. The lens employed in the CU-5 system is not suitable, however, and has to be replaced by a shorter focal length lens. Experimentally it was found that an f/11 aperture allowed reasonably fast prints, and gave a depth of focus of about 0.020 inches (0.5 mm) which allowed reasonable distribution of design tolerances. The lens employed is a Fuji 10.3 mm f/2.5 lens stopped down to f/11. These elements, assembled with one another, provide the correct magnification of about 26×.

In the preferred embodiment of the invention, the film pack size is so chosen that it allows the placement of six images onto the format, i.e., the image of a given microdot occupies only about one sixth of a single film frame, thus easing operation inasmuch as the precise location of the camera with respect to the microdot is no longer very critical. The exposure time is a function of illumination, i.e., the brighter the object, the shorter will be the exposure time. The preferred embodiment of the invention illuminates the microdot by means of two lens-end lamps 48, 49, mounted respectively on pillars 50, 51 that are attached to and upstanding from a base plate portion of fixture 42. The lamps 48, 49 are General Electric type 2601, the lamps being placed on both sides of the lens to achieve uniformity of illumination. The lamp rating is preferably selected to allow the lamps to be operated with either battery or with line power.

While I have thus described preferred embodiments of the present invention, variations will be apparent to those skilled in the art. It must therefore be understood that the foregoing description is intended to be illustrative only and not limitative of the present invention, and all such variations and modifications as are in accord with the principles described are meant to fall within the scope of the appended claims.

Having thus described my invention, I claim:

1. A method of enabling photographic identification of a human subject by use of a camera having a lens of predetermined fixed focal length, comprising the steps of placing a clamp on the tooth of a human subject to be identified to establish a reference plane that is generally parallel to and spaced outwardly from a buccal face of said tooth;

inserting an end-cutting burr into a dental hand piece;

adjusting the position of said burr in said hand piece so that the burr protrudes outwardly of said hand piece by a predetermined fixed distance that is related to the fixed focal length of the camera lens which is to be used in effecting said photographic identification, said adjusting step being effected by placing an elongated cylindrical spacer onto said burr in surrounding relation to said burr and thereafter varying the position of said burr in said handpiece by a distance which is equal to the length of said cylindrical spacer, plus the distance between said reference plane and said tooth face established by said clamp, plus a predetermined depth of a recess that is to be drilled into said tooth face;

positioning the hand piece relative to said clamp with said spacer on said burr and with the burr so adjusted thereafter moving said hand piece toward said tooth face and clamp until the end of the spacer remote from the hand piece engages an outer surface of said clamp so as thereby to drill a recess of said predetermined depth into said tooth face; and placing a microdot bearing identifying information thereon at the bottom of said recess and securing said microdot in place thereby to fix said microdot in place at a location that is spaced inwardly of the buccal face of the tooth by a precise distance that is related to said fixed focal length of the camera lens.

2. The method of claim 1 wherein said clamp includes a plate which covers said buccal face of said tooth and which has a hole therein through which said burr is passed during said drilling step, the surface of said plate remote from said tooth face constituting said reference plane.

3. The method of claim 1 including the further step of using a camera having a lens of predetermined fixed focal length to make an enlarged photographic image of said microdot while said microdot remains in place at the bottom of said recess.

4. The method of claim 3 wherein said camera includes a fixture extending forwardly of said lens by a distance which is related to the focal length of said lens and the depth of said recess, said step of photographing including the step of positioning said camera adjacent said tooth by bringing a predetermined portion of said fixture into engagement with the tooth to accurately locate the focal plane of said camera lens at said microdot before said camera is operated to photograph said microdot.

5. The method of claim 4 wherein said predetermined portion of said fixture comprises a clamp which is used to engage the tooth to properly locate the lens of said camera relative to said microdot.

6. A method of providing photographic identification of a human subject by use of a camera having a fixed focus lens of known focal length, comprising the steps of inserting an end-cutting burr into a dental hand piece;

adjusting the position of said burr so that the end-cutting portion thereof protrudes outwardly of said hand piece by a precise distance that is accurately related to the focal length of said camera lens;

using the dental hand piece with the burr so positioned to drill a recess of predetermined depth, accurately related to the focal length of said camera lens, into the buccal face of a tooth of the human subject;

placing a microdot containing identifying information at the bottom of said recess in a plane that is substantially parallel to and inward of the buccal face of said tooth, and then filling a transparent bonding medium into said recess to cover said microdot; and when identification of said human subject is desired, photographing said microdot through said transparent bonding medium with said camera, to produce an enlarged photographic image of said microdot, by locating the lens of the camera at a predetermined position relative to said buccal face of said tooth, the lens of said camera being a fixed focus lens having a focal length that corresponds to the distance between said lens and said buccal face of said tooth plus the predetermined depth of said recess whereby the focal plane of said lens is substantially coincident with the plane in which said microdot is located when said camera lens is at said predetermined position.

7. The method of claim 6 wherein said camera includes a fixture extending forwardly of said lens, said fixture having an element thereon which defines the proper spacing between said lens and said tooth for taking a focused photographic image of said microdot, said photographing step including the step of moving said camera toward said tooth until said element engages said tooth before said camera is actuated to photograph said microdot.

8. The method of claim 7 wherein said element is a spring-biased clamp which is used to grasp said tooth before said microdot is photographed.

9. A calibration instrument for use in adjusting the position of a burr in a dental hand piece to permit the drilling of a recess having a precise predetermined depth, said instrument comprising a body member having positioning means thereon for properly locating said body member relative to a dental drill having a burr therein, the interior of said body member including an interior open-ended channel that is in alignment with the burr when said dental hand piece is properly located relative to said body member, one open end of said channel being adapted to receive the burr, a sleeve member in thread engagement with said body member in coaxial relation with said channel, said sleeve member including a slidable pin therein in alignment with said channel, the other open end of said channel being adapted to receive one end of said slidable pin, said pin being adapted to be moved slidably relative to said sleeve member to cause said one end of said pin to be slid into said channel and into engagement with the free end of the burr to define a reference position of the burr relative to said sleeve member, means for selectively locking said pin against slidable movement relative to said sleeve member to fix said reference position, and manually engageable means on said sleeve member for turning said sleeve member relative to said body member whereby the threads between said body member and sleeve members move said sleeve member with said pin locked therein a predetermined distance relative to the free end of said burr for each 180° of turn of said sleeve member relative to said body member.

10. The calibration instrument of claim 9 wherein said positioning means comprises a recess in one face of said body member, said recess being coaxial with said channel.

11. The calibration instrument of claim 10 wherein said recess is a cylindrical recess sized to receive a cylindrical spacer member that is placed on said dental hand piece in surrounding relation to said burr prior to use of said calibration instrument.

12. The calibration instrument of claim 9 wherein said locking means is a set screw which is threaded into said sleeve member for selective engagement with said slidable pin.

13. The calibration instrument of claim 9 wherein the other end of said slidable pin extends through and to the exterior of said sleeve member to provide a portion of said pin which can be grasped manually to slide said pin relative to said sleeve member.

* * * * *